(12) United States Patent
Vangara et al.

(10) Patent No.: US 10,172,833 B2
(45) Date of Patent: *Jan. 8, 2019

(54) SUBLINGUAL ONDANSETRON SPRAY

(71) Applicant: Insys Development Company, Inc., Chandler, AZ (US)

(72) Inventors: Kiran Kumar Vangara, Phoenix, AZ (US); Chandeshwari Shivani Chilampalli, Phoenix, AZ (US); Venkat R. Goskonda, Phoenix, AZ (US)

(73) Assignee: INSYS DEVELOPMENT COMPANY, INC., Chandler, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/230,633

(22) Filed: Aug. 8, 2016

(65) Prior Publication Data

US 2017/0042861 A1 Feb. 16, 2017

Related U.S. Application Data

(60) Provisional application No. 62/203,409, filed on Aug. 11, 2015, provisional application No. 62/342,286, filed on May 27, 2016.

(51) Int. Cl.
| | | |
|---|---|---|
| *A61K 47/10* | (2017.01) | |
| *A61K 31/4178* | (2006.01) | |
| *A61K 9/00* | (2006.01) | |
| *A61K 47/12* | (2006.01) | |
| *A61K 9/08* | (2006.01) | |

(52) U.S. Cl.
CPC .......... *A61K 31/4178* (2013.01); *A61K 9/006* (2013.01); *A61K 9/08* (2013.01); *A61K 47/10* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 5,166,145 | A | 11/1992 | Jao et al. |
| 5,712,302 | A | 1/1998 | Young |
| 5,785,989 | A | 7/1998 | Stanley |
| 5,854,270 | A | 12/1998 | Gambhin |
| 6,063,802 | A | 5/2000 | Winterborn |
| 6,193,985 | B1 | 2/2001 | Sonne |
| 6,383,471 | B1 | 5/2002 | Chen |
| 6,555,546 | B2 | 4/2003 | Megens |
| 6,676,931 | B2 | 1/2004 | Dugger |
| 6,998,110 | B2 | 2/2006 | Dugger |

(Continued)

OTHER PUBLICATIONS

Verma et al. "An overview on Buccal Drug Delivery System", IJPSR (2011), vol. 2, issue 6, pp. 1301-1321.*

(Continued)

*Primary Examiner* — Ernst V Arnold
*Assistant Examiner* — Kyung S Chang
(74) *Attorney, Agent, or Firm* — Wood, Phillips, Katz, Clark & Mortimer

(57) ABSTRACT

The invention is directed to sublingual spray formulations containing ondansetron, a pharmaceutically acceptable salt thereof, and a solvent consisting of ethanol and glycerin, suitable for administration to humans, and methods for treatment with sublingual formulations.

16 Claims, 1 Drawing Sheet

(56) References Cited

U.S. PATENT DOCUMENTS

| | | | |
|---|---|---|---|
| 7,022,712 B2 | 4/2006 | Yalkowsky | |
| 7,229,642 B2 | 6/2007 | Fassihi | |
| 2004/0136914 A1* | 7/2004 | Dugger, III | A61K 31/4178 424/44 |
| 2004/0141923 A1 | 7/2004 | Dugger, III et al. | |
| 2007/0261695 A1 | 11/2007 | Kottayil et al. | |
| 2008/0188480 A1 | 8/2008 | Black | |
| 2009/0010992 A1 | 1/2009 | Palmer et al. | |
| 2011/0171140 A1 | 7/2011 | Illum et al. | |
| 2011/0171273 A1 | 7/2011 | Blondino et al. | |
| 2012/0064094 A1 | 3/2012 | Chabbert et al. | |
| 2013/0115294 A1 | 5/2013 | First | |
| 2013/0123179 A1 | 5/2013 | Gupta | |
| 2013/0178463 A1 | 7/2013 | Damaj | |
| 2014/0148491 A1* | 5/2014 | Valia | A61K 31/4178 514/397 |

OTHER PUBLICATIONS

Patel et al., "Sublingual route for the system delivery of ondansetron," International Journal of Drug Development and Research, Insight Medical Publishing, 2011, pp. 1-11. (Year: 2011).*

International Search Report for corresponding PCT application No. PCT/US2014/065646 published on Jan. 26, 2015.

Ni N et al., Solubilization and preformulation of carbendazim, Int J Pharm., Sep. 5, 2002, 244(1-2), 99-104.

International Preliminary Report on Patentability for corresponding PCT application No. PCT/US2014/065646 published on May 17, 2016.

* cited by examiner

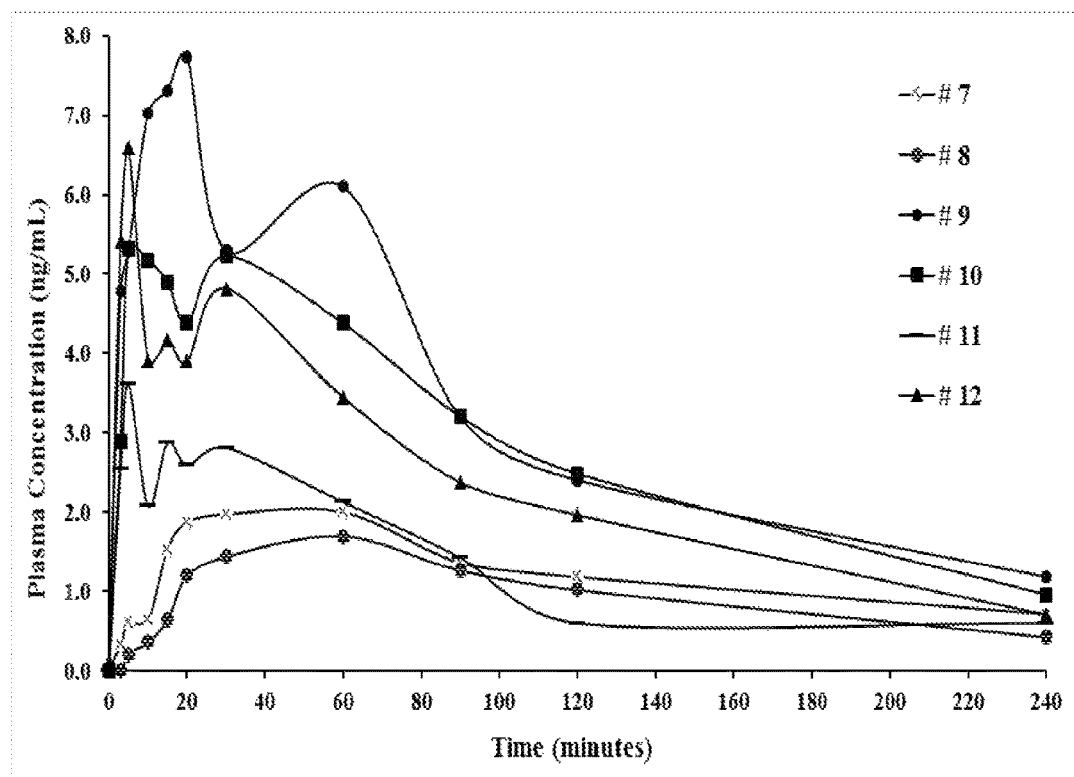

SUBLINGUAL ONDANSETRON SPRAY

FIELD OF THE INVENTION

The invention is directed to sublingual spray formulations containing ondansetron, or a pharmaceutically acceptable salt thereof, and a solvent consisting of ethanol and glycerin, suitable for administration to humans, and methods for treatment with sublingual formulations.

BACKGROUND OF THE INVENTION

Ondansetron is a serotonin 5-HT3 receptor antagonist with the following structure:

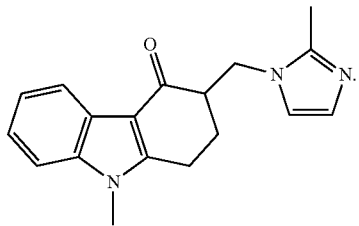 [SMILES: Cc1nccn1CC1CCc2c(c3ccccc3n2C)C1=O]

Ondansetron's primary use is as an antiemetic (to treat nausea and vomiting) following cancer treatments such as chemotherapy, surgery and/or radiation. Ondansetron works by reducing the activity of the vagus nerve which then deactivates the vomiting center in the medulla oblongata. Ondansetron also blocks serotonin receptors in the chemoreceptor trigger zone.

Ondansetron is currently available from GlaxoSmithKline as a film coated tablet, an oral solution, as an injection (Zofran®), and an orally disintegrating tablet (Zofran ODT®). Ondansetron is also available as an oral soluble film (Zuplenz®) from Vestiq Pharmaceuticals.

U.S. Pat. No. 6,998,110 discloses a method for administering a composition, such as ondansetron, to a mammal through the oral mucosa. This patent teaches that a polar solvent and a propellant are required. Although U.S. Pat. No. 6,676,931 teaches a propellant free ondansetron composition, this patent requires the use of a pharmacologically acceptable polar solvent in an amount of 19 to 90 weight percent and flavoring agent in an amount of 0.1 to 10 weight percent of the total composition.

U.S. Pat. No. 5,854,270 is directed to a liquid ondansetron formulation that includes a sorbitol-containing sweetener and has a pH of from 2 to 5. U.S. Pat. No. 6,555,546 discloses a formulation which may contain ondansetron and polyethylene glycol (PEG)-electrolyte solution for use in treating constipation or for accelerating intestinal lavage. However, these formulations fail to provide a sublingual formulation that has quick-onset and is storage stable.

"Sublingual" means "under the tongue" and refers to administration of a substance via the mouth in such a way that the substance is rapidly absorbed via the blood vessels under the tongue. A sublingual formulation is desirable because it bypasses hepatic first pass metabolic processes which provide better bioavailability, rapid onset of action, and higher patient compliance. Dysphagia (difficulty in swallowing) is common among in all ages of people and more in pediatric, geriatric, and psychiatric patients. In terms of permeability, the sublingual area of oral cavity is more permeable than buccal area. Sublingual drug administration is applied in field of cardiovascular drugs, steroids, enzymes and barbiturates.

While there are various ondansetron formulations currently available, there is still a need in the art for a rapid onset, storage stable, sublingual spray formulation containing ondansetron, or a pharmaceutically acceptable salt thereof.

SUMMARY OF THE INVENTION

In one aspect, the present invention is directed to sublingual spray formulations comprising from about 1 to about 15% w/w ondansetron or a pharmaceutically acceptable salt thereof, and a solvent consisting of ethanol and glycerin.

In another aspect, the formulation of the invention is a liquid, preferably a simple solution.

In another aspect, the present invention is directed to sublingual spray formulations comprising from about 1 to about 15% w/w ondansetron or a pharmaceutically acceptable salt thereof, and a solvent consisting of ethanol and glycerin, wherein the formulation is substantially free of propellant.

In another aspect, the present invention is directed to sublingual spray formulations comprising from about 1 to about 15% w/w ondansetron or a pharmaceutically acceptable salt thereof, and a solvent consisting of ethanol and glycerin, wherein the formulation is substantially free of water.

In another aspect, the present invention is directed to sublingual spray formulations comprising from about 1 to about 15% w/w ondansetron or a pharmaceutically acceptable salt thereof, a solvent consisting of ethanol and glycerin, and water.

In another aspect, the present invention is directed to sublingual spray formulations comprising from about 1% to about 15% w/w ondansetron or a pharmaceutically acceptable salt thereof and a solvent comprising ethanol and propylene glycol, caprylic acid and menthol, wherein % w/w is of the total formulation.

In another aspect, the present invention is directed to sublingual spray formulations comprising from about 1 to about 15% w/w ondansetron or a pharmaceutically acceptable salt thereof, a solvent consisting of ethanol and glycerin, and a permeation enhancer, preferably selected from the group consisting of menthol, caprylic acid and a combination thereof.

In another aspect, the present invention is directed to sublingual spray formulations comprising from about 1 to about 15% w/w ondansetron or a pharmaceutically acceptable salt thereof, a solvent consisting of ethanol and glycerin, and a pharmaceutically acceptable sweetener.

In another aspect, the present invention is directed to sublingual spray formulations comprising from about 1 to about 15% w/w ondansetron or a pharmaceutically acceptable salt thereof, a solvent consisting of ethanol and glycerin, and sucralose.

In another aspect, the present invention is directed to sublingual spray formulations comprising from about 1 to about 15% w/w ondansetron or a pharmaceutically acceptable salt thereof, and a solvent consisting of ethanol and glycerin, wherein the formulation is substantially free of water and wherein the formulation is capable of producing a droplet size distribution wherein the mean Dv(10) is from about 10 to about 35 microns during administration.

In another aspect, the present invention is directed to sublingual spray formulations comprising from about 1 to about 15% w/w ondansetron or a pharmaceutically acceptable salt thereof, and a solvent consisting of ethanol and glycerin, wherein the formulation is substantially free of water and wherein the formulation is capable of producing a droplet size distribution wherein the mean Dv(50) is from about 40 to about 200 microns during administration.

In another aspect, the present invention is directed to sublingual spray formulations comprising from about 1 to about 15% w/w ondansetron or a pharmaceutically acceptable salt thereof, and a solvent consisting of ethanol and glycerin, wherein the mean Dv(90) is from about 150 to about 700 microns during administration.

In another aspect, the present invention is directed to sublingual spray formulations comprising from about 1 to about 15% w/w ondansetron or a pharmaceutically acceptable salt thereof, and a solvent consisting of ethanol and glycerin, and wherein the formulation is capable of producing a spray plume wherein a mean ovality ratio is from about 1.0 to about 2.0.

In another aspect, the present invention is directed to sublingual spray formulations comprising from about 1 to about 15% w/w ondansetron or a pharmaceutically acceptable salt thereof, and a solvent consisting of ethanol and glycerin, and wherein the formulation is capable of producing a spray plume wherein a mean width is from about 20 to about 40 millimeters.

In another aspect, the present invention is directed to sublingual spray formulations comprising from about 1 to about 15% w/w ondansetron or a pharmaceutically acceptable salt thereof, wherein the formulation is capable of producing a spray plume wherein a mean angle is from about 25 to about 65 degrees.

In a preferred aspect, the present invention is directed to sublingual spray formulations comprising:

ondansetron or a pharmaceutically acceptable salt thereof at a concentration from about 1% to about 15% w/w; and a solvent comprising, consisting of, or consisting essentially of ethanol at a concentration from about 10% to about 80% w/w and glycerin at a concentration from about 10% to about 80% w/w.

In a preferred aspect, the present invention is directed to sublingual spray formulations comprising:

ondansetron or a pharmaceutically acceptable salt thereof at a concentration from about 1% to about 15% w/w;

a solvent consisting of ethanol at a concentration from about 10% to about 80% w/w and glycerin at a concentration from about 10% to about 80% w/w; and a permeation enhancer selected from the group consisting of menthol at a concentration from about 0.01% to about 8% w/w, caprylic acid at a concentration from about 0.1% to about 10% w/w or a combination thereof.

In a preferred aspect, the present invention is directed to sublingual spray formulations comprising:

ondansetron or a pharmaceutically acceptable salt thereof at a concentration from about 1% to about 15% w/w;

a solvent consisting of ethanol at a concentration from about 10% to about 80% w/w and glycerin at a concentration from about 10% to about 80% w/w; and a permeation enhancer selected from the group consisting of menthol at a concentration from about 0.01% to about 8% w/w, caprylic acid at a concentration from about 0.1% to about 10% w/w or a combination thereof, wherein the formulation is substantially free of water.

In a preferred aspect, the present invention is directed to sublingual spray formulations comprising:

ondansetron or a pharmaceutically acceptable salt thereof at a concentration from about 1% to about 15% w/w;

a solvent consisting of ethanol at a concentration from about 10% to about 80% w/w and glycerin at a concentration from about 10% to about 80% w/w;

a permeation enhancer selected from the group consisting of menthol at a concentration from about 0.01% to about 8% w/w, caprylic acid at a concentration from about 0.1% to about 10% w/w or a combination thereof; and water at a concentration from about 1% to about 50% w/w.

In a more preferred aspect, the present invention is directed to sublingual spray formulations comprising:

ondansetron or a pharmaceutically acceptable salt thereof at a concentration from about 3% to about 11% w/w;

a solvent consisting of ethanol at a concentration from about 30% to about 60% w/w and glycerin at a concentration from about 30% to about 48% w/w; and a permeation enhancer selected from the group consisting of menthol at a concentration from about 0.05% to about 5% w/w, caprylic acid at a concentration of about 2% w/w and a combination thereof.

In a more preferred aspect, the present invention is directed to sublingual spray formulations comprising:

ondansetron or a pharmaceutically acceptable salt thereof at a concentration from about 3% to about 11% w/w;

a solvent consisting of ethanol at a concentration from about 30% to about 60% w/w and glycerin at a concentration from about 30% to about 48% w/w; and a permeation enhancer selected from the group consisting of menthol at a concentration from about 0.05% to about 5% w/w, caprylic acid at a concentration of about 2% w/w and a combination thereof, wherein the formulation is substantially free of water.

In a more preferred aspect, the present invention is directed to sublingual spray formulations comprising:

ondansetron or a pharmaceutically acceptable salt thereof at a concentration from about 3% to about 11% w/w;

a solvent consisting of ethanol at a concentration from about 30% to about 60% w/w and glycerin at a concentration from about 30% to about 48% w/w;

a permeation enhancer selected from the group consisting of menthol at a concentration from about 0.05% to about 5% w/w, caprylic acid at a concentration of about 2% w/w and a combination thereof; and from about 1% to about 50% water.

In yet another preferred aspect, the present invention is directed to sublingual spray formulations comprising:

ondansetron at a concentration from about 3% to about 11% w/w;

ethanol at a concentration from about 40% to about 60% w/w;

propylene glycol at a concentration from about 1% to about 10% w/w;

menthol at a concentration from about 0.05% to about 5% w/w; and caprylic acid at a concentration from about 0.5% to about 5% w/w.

In yet another preferred aspect, the present invention is directed to sublingual spray formulations comprising:

ondansetron at a concentration from about 3% to about 5% w/w;

ethanol at a concentration of about 50% w/w;

propylene glycol at a concentration of about 5% w/w;

menthol at a concentration of about 0.5% w/w; and
caprylic acid at a concentration of about 2% w/w.

In a yet more preferred aspect, the present invention is directed to sublingual spray formulations comprising:
ondansetron or a pharmaceutically acceptable salt thereof at a concentration of about 4.24% w/w;
a solvent consisting of ethanol at a concentration of about 50% and glycerin at a concentration of about 30% w/w; and
a permeation enhancer consisting of menthol at a concentration of about 0.5% w/w and caprylic acid at a concentration of about 2% w/w.

In a yet more preferred aspect, the present invention is directed to sublingual spray formulations comprising:
ondansetron or a pharmaceutically acceptable salt thereof at a concentration of about 4.24% w/w;
a solvent consisting of ethanol at a concentration of about 50%, glycerin at a concentration of about 30% w/w; and
a permeation enhancer consisting of menthol at a concentration of about 0.5% w/w;
caprylic acid at a concentration of about 2% w/w;
a pharmaceutically acceptable sweetener consisting of sucralose at a concentration of about 0.6% w/w;
a preservative consisting about 0.001% w/w edetate disodium dihydrate and about 0.01% w/w benzalkonium chloride; and
about 0.08% w/w of strawberry flavor.

In another aspect, the present invention is directed to a method for treating or preventing nausea and emesis in humans associated with chemotherapy, radiation or surgery for cancer treatment comprising administering a sublingual spray formulation of the present invention to a patient in need thereof.

In another aspect, the present invention is directed to a method for treating or preventing nausea and emesis in humans associated with chemotherapy, radiation or surgery for cancer treatment comprising administering about 50 to about 400 µL of a sublingual spray formulation of the present invention to a patient in need thereof.

In another aspect, the present invention is directed to a method for treating or preventing nausea and emesis in humans associated with chemotherapy, radiation or surgery for cancer treatment comprising administering about 100 to about 200 µL of a sublingual spray formulation of the present invention to a patient in need thereof.

BRIEF DESCRIPTION OF THE DRAWINGS

FIG. 1. shows pharmacokinetic profiles of ondansetron sublingual formulation administered to Yucatan mini-pigs and illustrates superior performance of formulations containing caprylic acid.

DETAILED DESCRIPTION OF THE INVENTION

Applicants unexpectedly discovered a sublingual ondansetron spray formulation, which has improved storage stability and excellent spray characteristics.

Definitions

As used herein, "ondansetron" refers to the base or a pharmaceutically acceptable salt, ester, derivative, or prodrug thereof.
Pharmaceutically acceptable salts that can be used in accordance with the current invention include but are not limited to hydrochloride salts. In preferred embodiments the pharmaceutically acceptable salt is hydrochloride.

As used herein, "nausea" refers to the sensation of unease and discomfort in the upper stomach with an involuntary urge to vomit.

As used herein, "emesis" refers to the action of vomiting.

As used herein, "chemotherapy" refers to administering one or more cytotoxic anti-neoplastic drugs to a cancer patient as part of a standardized treatment regimen.

As used herein, "free of propellant" refers to a sublingually administered formulation that is not administered using compressed gas.

As used herein, "substantially free of water" refers to a sublingual spray which contains less than 0.5% w/w water.

As used herein the term "patient" refers, but is not limited to, a person that is being treated for nausea and emesis.

As used herein the term "pharmaceutically acceptable" refers to ingredients that are not biologically or otherwise undesirable in a sublingual dosage form.

As used herein the term "effective amount" refers to the amount necessary to treat a patient in need thereof.

As used herein "% w/w" and "percent w/w" refer to the percent weight of the total formulation.

As used herein, all numerical values relating to amounts, weights, and the like, that are defined as "about" each particular value is plus or minus 10%. For example, the phrase "about 10% w/w" is to be understood as "9% to 11% w/w." Therefore, amounts within 10% of the claimed value are encompassed by the scope of the claims.

Compositions of the Invention

In a preferred aspect, the present invention is directed to sublingual spray formulations comprising:
ondansetron or a pharmaceutically acceptable salt thereof at a concentration from about 1% to about 15% w/w;
a solvent consisting of ethanol at a concentration from about 10% to about 80% w/w and glycerin at a concentration from about 10% to about 80% w/w; and
a permeation enhancer selected from the group consisting of menthol at a concentration from about 0.01% to about 8% w/w, caprylic acid at a concentration from about 1% to about 10% w/w or a combination thereof.

In a more preferred aspect, the present invention is directed to sublingual spray formulations comprising:
ondansetron or a pharmaceutically acceptable salt thereof at a concentration from about 8% to about 11% w/w;
a solvent consisting of ethanol at a concentration from about 40% to about 48% w/w and glycerin at a concentration from about 40% to about 48% w/w; and
menthol at a concentration from about 2% to about 5% w/w.

In a yet more preferred aspect, the present invention is directed to sublingual spray formulations comprising:
ondansetron or a pharmaceutically acceptable salt thereof at a concentration from about 3% to about 11% w/w;
a solvent consisting of ethanol at a concentration from about 30% to about 50% w/w and glycerin at a concentration from about 30% to about 48% w/w; and
a permeation enhancer selected from the group consisting of menthol at a concentration from about 0.05% to about 5% w/w, caprylic acid at a concentration of about 2% w/w and a combination thereof.

In a yet more preferred aspect, the present invention is directed to sublingual spray formulations comprising:
ondansetron or a pharmaceutically acceptable salt thereof at a concentration of about 4.24% w/w;

a solvent consisting of ethanol at a concentration of about 50% and glycerin at a concentration of about 30% w/w; and a permeation enhancer consisting of menthol at a concentration of about 0.5% w/w and caprylic acid at a concentration of about 2% w/w;

a pharmaceutically acceptable sweetener consisting of sucralose at a concentration of about 0.6% w/w; and a preservative consisting about 0.001% w/w edetate disodium dihydrate and about 0.01% w/w benzalkonium chloride.

In some embodiments, the formulations of the present invention may contain a preservative. Preservatives include, but are not limited to, methyl paraben, ethyl paraben, butyl paraben, propyl paraben, sodium benzoate, benzoic acid, edetate disodium dihydrate, benzalkonium chloride ("BKC") or a mixture thereof. Preferred preservatives are edetate disodium dihydrate and BKC.

When a preservative is used, the effective amount of the preservative is from about 0.01% to about 0.5% w/w of the formulation.

In some embodiments, the formulations of the present invention may also contain a permeation enhancer. Permeation enhancers include, but are not limited to, menthol, menthol, limonene, carvone, transcutol, oleic acid, triacetin, polysorbate 80, polyoxyl 35 hydrogenated castor oil, polyvinylpyrrolidone, caprylocaproyl, fatty acids including caproic acid, enanthic acid, caprylic acid, pelargonic acid, capric acid, undecylenic acid, lauric acid, myristic acid, pentadecylic acid, palmitic acid, margaric acid, oleic acid, stearic acid, nonadecylic acid, linoleic acid, arachidic acid and arachidonic acid, medium chain glycerides, decanoyl glycerides, octanoyl glycerides, caprylic/capric triglyceride, caprylic/capric/linoleic triglyceride, macrogol-8 glyceride, sodium glycocholate, sodium lauryl sulphate, sodium taurocholate, triethyl citrate, mannitol, disodium laureth sulfosuccinate, N-[8-(2-hydroxybenzoyl)amino]caprylate, n-dodecyl β-D-maltoside, glyceryl monosterate, sodium caprate, and dodecyl dimethyl amino propionate. One presently preferred permeation enhancer is menthol and caprylic acid.

When a permeation enhancer is used, the effective amount of the permeation enhancer is from about 0.01% to about 10.0% w/w of the formulation, preferably from about 0.05% to about 5.0% w/w.

In some embodiments, the formulations of the present invention may also contain a flavoring agent. Flavoring agents include, but are not limited to, menthol, fruit punch flavor, strawberry flavor, cherry flavor, raspberry flavor, mint flavor, orange oil, spearmint oil, citrus oil, peppermint oil, cinnamon oil, anise oil, or a mixture thereof. Preferred flavoring agents are menthol and fruit punch flavor.

When a flavoring agent is used, the effective amount of the flavoring agent is from about 0.01% to about 0.5% w/w of the formulation.

When menthol is used in a formulation of the present invention in amounts of 0.5% w/w or more the menthol is both a flavoring agent and a permeation enhancer.

In some embodiments, the formulations of the present invention may also contain a sweetener. Sweeteners include sucralose, sucrose, aspartame, neotame, saccharin, dextrose, mannitol, glycerin, xylitol, or a combination thereof. A preferred sweetener is sucralose.

When a sweetener is used, the effective amount of the sweetener is from about 0.01% to about 0.5% w/w of the formulation.

The following preferred embodiments and examples are intended to illustrate the present invention and to teach one of ordinary skill in the art how to use the formulations of the invention. They are not intended to be limiting in any way.

PREFERRED EMBODIMENTS

TABLE 1

Sublingual Ondansetron Spray Formulations

| | Formulation (% w/w) | | | | | |
|---|---|---|---|---|---|---|
| | #1 | #2 | #3 | #4 | #5 | #6 |
| Ondansetron (Hydrochloride Dihydrate) | 10.80 | 10.80 | 5.00 | 10.10 | 10.10 | 10.00 |
| Ethanol | 44.00 | 42.00 | 44.50 | 42.00 | 43.00 | 42.00 |
| Glycerin | 43.96 | 41.01 | 44.46 | 41.78 | 43.28 | 42.28 |
| Sucralose | 1.00 | 1.00 | 1.00 | 1.00 | 1.00 | 1.0 |
| L-Menthol | 0.05 | 5.00 | 5.00 | 5.00 | 2.50 | 2.50 |
| Methyl Paraben | 0.02 | 0.02 | 0.02 | 0.10 | 0.10 | 0.10 |
| Propyl Paraben | 0.02 | 0.02 | 0.02 | 0.02 | 0.02 | 0.02 |
| Fruit Punch Flavor | 0.15 | 0.15 | | | | |
| Water | | | | | | 2.0 |

TABLE 2

Additional Sublingual Ondansetron Spray Formulations

| | Formulation (% w/w) | | | | | |
|---|---|---|---|---|---|---|
| | #7 | #8 | #9 | #10 | #11 | #12 |
| Ondansetron (Hydrochloride Dihydrate) | 10.71 | 4.22 | 3.72 | 4.56 | 4.1 | 4.24 |
| Ethanol | 42.8 | 31.21 | 50 | 50 | 40 | 50 |
| Propylene Glycol | | 15 | 5 | 5 | | |
| Glycerin | 42.87 | | | | 40 | 30 |
| Sucralose | 1 | 0.6 | 0.6 | 0.6 | 0.6 | 0.6 |
| L-Menthol | 2.5 | 0.05 | 0.5 | 0.5 | 0.5 | 0.5 |
| Edetate disodium dihydrate | | | 0.001 | 0.001 | 0.001 | 0.001 |
| Benzalkonium chloride | | | 0.01 | 0.01 | 0.01 | 0.01 |
| Methyl paraben/ Propyl paraben | 0.12 | 0.04 | | | | |
| Caprylic acid | | | 2 | 2 | 2 | 2 |
| Flavor | | 0.15 | 0.08 | 0.08 | 0.08 | 0.08 |
| Water | | 48.73 | 38.09 | 37.25 | 12.71 | 12.56 |

EXAMPLES

Method of Making the Formulations

Excipients were first dissolved in either the ethanol or the purified water based on their solubility by mixing. Water and alcohol phase were then combined together and mixed to make homogenous solution. Ondansetron hydrochloride dihydrate was then added to the excipients solution and mixed until dissolved.

Example 1: Stable Ondansetron Formulations

Stability Data

Formulations #1-#3 of Table 1 were subjected to stability test at 40° C.±2° C./75%±5% RH and 25° C.±2° C./60%±5% RH. At predetermined time points samples were pulled and analyzed for stability. Assay and impurities were detected using high performance liquid chromatography with an ultraviolet detector. The assay was performed at 216 nm and indicated as a % of initial concentration. For all impurities, analysis was performed at 216 nm and expressed as a % area. Stability data of these formulations are summarized in Tables 3-8.

TABLE 3

Stability Data for Sublingual Ondansetron Spray Formulation #1 stored at 40° C. ± 2° C. under 75% ± 5% Relative Humidity

| 40° C. | Formulation #1 | | | |
|---|---|---|---|---|
| | T0 | 1 Month | 3 Months | 4 Months |
| Assay (% of initial concentration) | 100 | 100.93 | 101.97 | 100.54 |
| % Impurity D | 0.02 | 0.04 | 0.07 | 0.06 |
| % Impurity F | ND | ND | BQL | BQL |
| Total Impurities (% Area) | 0.02% | 0.04% | 0.07% | 0.06% |

TABLE 4

Stability Data for Sublingual Ondansetron Spray Formulation #2 stored at 40° C. ± 2° C. under 75% ± 5% Relative Humidity

| 40° C. | Formulation #2 | | | |
|---|---|---|---|---|
| | T0 | 1 Month | 3 Months | 4 Months |
| Assay (% of initial concentration) | 100 | 100.66 | 101.56 | 100.82 |
| % Impurity D | 0.02 | 0.04 | 0.07 | 0.07 |
| % Impurity F | ND | ND | ND | BQL |
| Total Impurities (% Area) | 0.02% | 0.04% | 0.07% | 0.07% |

TABLE 5

Stability Data for Sublingual Ondansetron Spray Formulation #3 stored at 40° C. ± 2° C. under 75% ± 5% Relative Humidity

| 40° C. | Formulation #3 | | | |
|---|---|---|---|---|
| | T0 | 1 Month | 2 Months | 3 Months |
| Assay (% of initial concentration) | 100 | 97.82 | 97.58 | 99.34 |
| % Impurity D | 0.03 | 0.04 | 0.04 | 0.05 |
| % Impurity F | ND | ND | ND | BQL |
| Total Impurities (% Area) | 0.03% | 0.04% | 0.04% | 0.05% |

TABLE 6

Stability Data for Sublingual Ondansetron Spray Formulation #1 stored at 25° C. ± 2° C. under 60% ± 5% Relative Humidity

| 25° C. | Formulation #1 | |
|---|---|---|
| | T0 | 3 Months |
| Assay (% of initial concentration) | 100 | 102.21 |
| % Impurity D | 0.02 | 0.03 |
| % Impurity F | ND | ND |
| Total Impurities (% Area) | 0.02% | 0.03% |

TABLE 7

Stability Data for Sublingual Ondansetron Spray Formulation #2 stored at 25° C. ± 2° C. under 60% ± 5% Relative Humidity

| 25° C. | Formulation #2 | |
|---|---|---|
| | T0 | 3 Months |
| Assay (% of initial concentration) | 100 | 102.55 |
| % Impurity D | 0.02 | 0.03 |
| % Impurity F | ND | ND |
| Total Impurities (% Area) | 0.02% | 0.03% |

TABLE 8

Stability Data for Sublingual Ondansetron Spray Formulation #3 stored at 25° C. ± 2° C. under 60% ± 5% Relative Humidity

| 25° C. | Formulation #3 | |
|---|---|---|
| | T0 | 3 Months |
| Assay (% of initial concentration) | 100 | 99.58 |
| % Impurity D | 0.03 | 0.03 |
| % Impurity F | ND | ND |
| Total Impurities (% Area) | 0.03% | 0.03% |

Results

Each formulation showed unexpected stability. After 3 months, formulation #1 had 0.07% w/w and 0.03% w/w total impurities at 40° C.±2° C./75%±5% relative humidity ("RH") and 25° C.±2° C./60%±5% RH, respectively; formulation #2 had 0.07% w/w and 0.03% w/w; and formulation #3 had 0.05% w/w and 0.03% w/w. Concentrations of any excipient used in formulations did not exceed maximum allowable daily dose recommended in FDA's inactive ingredient list. The stability of each formulation showed that all the excipients used in the formulations were compatible with Ondansetron.

Example 2: Spray Characteristics of Sublingual Ondansetron Formulations

Formulations #4 and #5 of Table 1 were used to evaluate spray characteristics of an ondansetron sublingual spray. The data for droplet size distribution and spray pattern are provided in Tables 9-20. All data was collected while formulations were at 25° C.

TABLE 9

Droplet Size Distribution of Formulation #4 at 3 cm

| 3 cm | Formulation #4 | | | |
|---|---|---|---|---|
| | Dv (10) | Dv (50) | Dv (90) | Span |
| Mean | 25.5 µm | 100.0 µm | 500.0 µm | 4.7 |
| Min | 24.6 µm | 91.5 µm | 456.2 µm | 4.6 |
| Max | 26.4 µm | 116.1 µm | 562.2 µm | 5 |

TABLE 10

Droplet Size Distribution of Formulation #4 at 6 cm

| 6 cm | Formulation #4 | | | |
|---|---|---|---|---|
|  | Dv (10) | Dv (50) | Dv (90) | Span |
| Mean | 28.3 μm | 65.7 μm | 389.1 μm | 5.2 |
| Min | 24.9 μm | 46.0 μm | 154.8 μm | 2.8 |
| Max | 31.1 μm | 89.4 μm | 537.1 μm | 7.2 |

TABLE 11

Droplet Size Distribution of Formulation #5 at 3 cm

| 3 cm | Formulation #5 | | | |
|---|---|---|---|---|
|  | Dv (10) | Dv (50) | Dv (90) | Span |
| Mean | 26.8 μm | 164.1 μm | 601.4 μm | 4.1 |
| Min | 25.0 μm | 103.1 μm | 526.8 μm | 2.4 |
| Max | 28.5 μm | 277.5 μm | 697.4 μm | 4.9 |

TABLE 12

Droplet Size Distribution of Formulation #5 at 6 cm

| 6 cm | Formulation #5 | | | |
|---|---|---|---|---|
|  | Dv (10) | Dv (50) | Dv (90) | Span |
| Mean | 27.7 μm | 73.5 μm | 581.4 μm | 7.6 |
| Min | 26.8 μm | 66.3 μm | 568.3 μm | 6.6 |
| Max | 28.8 μm | 82.8 μm | 605.3 μm | 8.7 |

TABLE 13

Spray Pattern of Formulation #4 at 3 cm

| 3 cm | Formulation #4 | | |
|---|---|---|---|
|  | Dmin | Dmax | Ovality Ratio |
| Mean | 16.4 mm | 20.9 mm | 1.3 |
| Min | 15.3 mm | 19.2 mm | 1.4 |
| Max | 17.9 mm | 22.3 mm | 1.2 |

TABLE 14

Spray Pattern of Formulation #4 at 6 cm

| 6 cm | Formulation #4 | | |
|---|---|---|---|
|  | Dmin | Dmax | Ovality Ratio |
| Mean | 22.3 mm | 30.5 mm | 1.4 |
| Min | 20.3 mm | 28.1 mm | 1.2 |
| Max | 24.2 mm | 32.5 mm | 1.5 |

TABLE 15

Spray Pattern of Formulation #5 at 3 cm

| 3 cm | Formulation #5 | | |
|---|---|---|---|
|  | Dmin | Dmax | Ovality Ratio |
| Mean | 16.3 mm | 22.9 mm | 1.4 |
| Min | 14.8 mm | 20.6 mm | 1.3 |
| Max | 17.8 mm | 24.2 mm | 1.6 |

TABLE 16

Spray Pattern of Formulation #5 at 6 cm

| 6 cm | Formulation #5 | | |
|---|---|---|---|
|  | Dmin | Dmax | Ovality Ratio |
| Mean | 22.7 mm | 32.6 mm | 1.4 |
| Min | 22.0 mm | 27.2 mm | 1.2 |
| Max | 23.7 mm | 37.2 mm | 1.7 |

TABLE 17

Plume Geometry of Formulation #4 at 3 cm

| 3 cm | Formulation #4 | |
|---|---|---|
|  | Width | Angle |
| Mean | 26.1 mm | 46.3 |
| Min | 23.5 mm | 42.3 |
| Max | 29 mm | 50.6 |

TABLE 18

Plume Geometry of Formulation #4 at 6 cm

| 6 cm | Formulation #4 | |
|---|---|---|
|  | Width | Angle |
| Mean | 29.3 mm | 27.3 |
| Min | 23.5 mm | 21.9 |
| Max | 38.6 mm | 35.7 |

TABLE 19

Plume Geometry of Formulation #5 at 3 cm

| 3 cm | Formulation #5 | |
|---|---|---|
|  | Width | Angle |
| Mean | 24.9 mm | 43.9 |
| Min | 19.0 mm | 33.5 |
| Max | 28.1 mm | 49.2 |

TABLE 20

Plume Geometry of Formulation #5 at 6 cm

| 6 cm | Formulation #5 | |
|---|---|---|
|  | Width | Angle |
| Mean | 34.2 mm | 31.7 |
| Min | 32.6 mm | 30.4 |
| Max | 35.3 mm | 32.5 |

A challenge of creating an ondansetron sublingual spray formulation is that it must be capable of producing spray droplets that are over 10 microns in diameter. Spray droplets 10 microns or smaller could be inhaled into the lungs. Sublingual formulations should be able to maintain a consistent droplet size throughout its shelf life.

Formulations #4 and #5 yielded excellent droplet sizes and spray patterns for sublingual administration. The testing also revealed that the formulation dose remained consistent when administered with a spray pump.

Example 3: Pharmacokinetics of Ondansetron Sublingual Spray Formulations in Mini-Pigs Study Design Protocol design was a single dose crossover study. Four or five healthy male Yucatan mini-pigs weighing approximately forty kilograms each were sublingually administered the ondansetron formulations. The mini-pigs were fasted overnight till four hours post administration. Each dosing was followed by a one-week washout period. Blood samples were taken prior to administration and 3, 5, 10, 15, 20, 30 min, 1, 2, 4, 8 and 24 hours post administration. Mini-pig plasma samples were measured for ondansetron concentrations via liquid chromatography-tandem mass spectrometry.

The following pharmacokinetic parameters were calculated: peak concentration in plasma ($C_{max}$), time to reach $C_{max}$ ($T_{max}$), and area under the concentration-time curve from time-zero to 24 hours post-dose ($AUC_{0-24h}$).

TABLE 21

Pharmacokinetic parameters of ondansetron sublingual spray in mini-pigs

| Formulation | $T_{max}$ (min) | $C_{max}$ (ng/mL) | $AUC_{0-24\,h}$ (ng*min/mL) |
|---|---|---|---|
| # 7 | 60 | 2.5 ± 1.9 | 340.6 ± 1.5 |
| # 8 | 60 | 1.9 ± 2.5 | 399.8 ± 2.1 |
| # 9 | 5 | 14.3 ± 2.1 | 1213.5 ± 1.4 |
| # 10 | 8 | 8.2 ± 1.6 | 1165.3 ± 1.2 |
| # 11 | 5 | 4.7 ± 1.4 | 567.7 ± 1.5 |
| # 12 | 3 | 8.9 ± 2.5 | 858.6 ± 1.2 |

$T_{max}$: median value
$C_{max}$ and $AUC_{0-24\,h}$: geometric mean ± geometric SD Results Pharmacokinetic profiles of ondansetron formulations tested in mini-pigs are showed in FIG. 1. The summary of ondansetron pharmacokinetic parameters after single-dose sublingual administration of ondansetron formulations to Yucatan mini-pigs under fasted conditions are summarized in Table 21. As shown, Formulations #9-12, which include caprylic acid and replaced parabens with edetate disodium dihydrate and benzalkonium chloride showed better pharmacokinetic performance, compared to Formulations #7 and #8. Specifically, Formulations #9-12 reached peak plasma concentration at least 7 times faster; achieved a much greater peak plasma concentration and achieved a greater area under the curve than Formulations #7 and #8. Notably, Formulation #12 reached maximum plasma concentration of 8.9 in only 3 minutes.

Example 4: Ondansetron Sublingual Spray Characterization

Formulations #12 Table 2 was used to evaluate spray characteristics of an ondansetron sublingual spray. The data for droplet size distribution and spray pattern are provided in Tables 22-25. All data was collected while formulations were at 25° C.

TABLE 22

Spray Pattern of Ondansetron Sublingual Spray at 3 cm

| SP 3 CM 25° C. | Dmin | Dmax | Ovality Ratio |
|---|---|---|---|
| Mean | 18.7 mm | 32.0 mm | 1.7 |
| Min | 17.6 mm | 31.5 mm | 1.7 |
| Max | 19.3 mm | 32.6 mm | 1.8 |

TABLE 23

Spray Pattern of Ondansetron Sublingual Spray at 6 cm

| SP 6 CM 25° C. | Dmin | Dmax | Ovality Ratio |
|---|---|---|---|
| Mean | 24.5 mm | 46.4 mm | 1.898 |
| Min | 22.7 | 40.3 | 1.61 |
| Max | 25.7 | 52.1 | 2.06 |

TABLE 24

Droplet Size Distribution of Ondansetron Sublingual Spray at 3 cm

| DSD 3 CM 25° C. | Dv (10) | Dv (50) | Dv (90) | Span |
|---|---|---|---|---|
| Mean | 16.9 μm | 42.1 μm | 195.9 μm | 4.3 |
| Min | 16.3 | 40.9 | 182.5 | 3.7 |
| Max | 17.5 | 44.4 | 216.2 | 4.9 |

TABLE 25

Droplet Size Distribution of Ondansetron Sublingual Spray at 6 cm

| DSD 6 CM 25° C. | Dv (10) | Dv (50) | Dv (90) | Span |
|---|---|---|---|---|
| Mean | 20.6 μm | 44.2 μm | 156.2 μm | 3.0 |
| Min | 19.2 | 41.28 | 112.4 | 2.071 |
| max | 21.94 | 47.73 | 234.6 | 4.485 |

A challenge of creating an ondansetron sublingual spray formulation is that it must be capable of producing spray droplets that are over 10 microns in diameter. Spray droplets 10 microns or smaller could be inhaled into the lungs. Sublingual formulations should be able to maintain a consistent droplet size throughout its shelf life.

Formulation #3 yielded excellent droplet sizes and spray patterns for sublingual administration. The testing also revealed that the formulation dose remained consistent when administered with a spray pump.

Example 5: Stability of Ondansetron Sublingual Spray Formulations

Formulations #7-#12 of Table 2 were subjected to stability test at various temperatures including 55° C.±2, 40° C.±2° C./75%±5% RH and 25° C.±2° C./60%±5% RH. At predetermined time points samples were pulled and analyzed for stability. Assay and impurities were detected using high performance liquid chromatography with an ultraviolet detector. The assay was performed at 216 nm and indicated as a % of initial concentration. For all impurities, analysis was performed at 216 nm and expressed as a % area. Stability data of these formulations are summarized in Tables 25-29.

TABLE 26

Stability data for ondansetron sublingual spray formulation# 7 stored at 40° C. ± 2° C. under 75% ± 5% relative humidity

| Formulation # 7 | | 40° C. | | |
|---|---|---|---|---|
| | RRT | Time Zero | 1 month | 2 months |
| Assay | | 101.8 | 101.4 | 104.0 |
| Impurity B | 1.13 | 0.09 | 0.05 | 0.05 |
| Impurity D | 1.78 | ND | ND | 0.06 |
| Total (% area) | | 0.09% | 0.05% | 0.10% |

TABLE 27

Stability data for ondansetron sublingual spray formulation# 8
stored at 40° C. ± 2° C. under 75% ± 5%
relative humidity and at 25° C. ± 2° C. under 60% ± 5% relative humidity Formulation # 8

|  |  | Time | 40° C. | | | 25° C. | |
|---|---|---|---|---|---|---|---|
|  | RRT | zero | 1 month | 3 months | 6 months | 3 months | 6 months |
| Assay |  | 101.2 | 102.5 | 101.8 | 103.7 | 100.9 | 101.9 |
| Impurity B | 1.13 | BQL | 0.05 | BQL | 0.06 | BQL | 0.07 |
| Impurity D | 1.78 | ND | ND | BQL | 0.06 | ND | ND |
| Total (% area) |  | BQL | 0.05% | BQL | 0.11% | BQL | 0.07% |

TABLE 28

Stability data for ondansetron sublingual spray formulation# 10 stored at 55° C.,
at 40° C. ± 2° C. under 75% ± 5% relative humidity and at 25° C. ± 2° C. under 60% ± 5% relative humidity Formulation # 10

|  |  | Time | 55° C. | | | 40° C. | | 25° C. | |
|---|---|---|---|---|---|---|---|---|---|
|  | RRT | zero | 1 week | 2 weeks | 1 month | 2 weeks | 1 month | 2 weeks | 1 month |
| Assay |  | 100 | 100.86 | 103.12 | 105.67 | 101.73 | 101.13 | 102.09 | 100.98 |
| Unknown Impurity 1 | 1.18 | 0.01 | ND | ND | ND | ND | ND | ND | ND |
| Impurity B | 1.13 | ND | ND | ND | 0.06 | ND | 0.03 | ND | 0.06 |
| Impurity D | 1.78 | 0.02 | 0.03 | 0.29 | 0.12 | 0.06 | 0.06 | 0.02 | 0.02 |
| Total (% area) |  | 0.04% | 0.05% | 0.29% | 0.18% | 0.06% | 0.08% | 0.02% | 0.08% |

TABLE 29

Stability data for ondansetron sublingual
spray formulation# 11 stored at 55° C.

Formulation # 11

|  |  |  | 55° C. | | 40° C. |
|---|---|---|---|---|---|
|  | RRT | Time Zero | 1 week | 2 weeks | 2 weeks |
| Assay |  | 100 | 97.98 | 98.78 | 99.05 |
| Impurity B | 1.13 | ND | 0.06 | ND | ND |
| Impurity D | 1.78 | 0.02 | 0.05 | 0.11 | 0.02 |
| Impurity F | 1.0* | ND | ND | 0.01 | 0.01 |
| Total (% area) |  | 0.02% | 0.11% | 0.12% | 0.03% |

*RRT to impurity F in impurity E and F method

TABLE 30

Stability data for ondansetron sublingual
spray formulation# 12 stored at 55° C.

Formulation # 12

|  |  |  | 55° C. | | 40° C. |
|---|---|---|---|---|---|
|  | RRT | Time Zero | 1 week | 2 weeks | 2 weeks |
| Assay |  | 100 | 101.62 | 99.93 | 101.09 |
| Unknown Impurity 1 | 1.12 | ND | 0.01 | ND | ND |
| Impurity B | 1.13 | ND | 0.02 | ND | ND |
| Impurity D | 1.78 | 0.02 | 0.02 | 0.07 | 0.02 |
| Impurity G | 0.96 | ND | ND | 0.01 | ND |
| Total (% area) |  | 0.02% | 0.05% | 0.08% | 0.02% |

Results

Each formulation showed unexpected stability. After 2 months at 40° C.±2° C./75%±5% relative humidity ("RH"), Formulation #7 had 0.1% total impurities. After 6 months at ° C.±2° C./75%±5% RH and 25° C.±2° C. under 60%±5% RH, Formulation #8 had 0.11% and 0.07% total impurities, respectively. After 1 month at 55° C.±2° C., 40° C.±2° C. under 75%±5% RH and at 25° C.±2° C. under 60%±5% RH, Formulation #10 had 0.18%, 0.08% and 0.08% total impurities, respectively. After 2 weeks at 55° C.±2° C. and 40° C.±2° C. under 75%±5% RH, Formulation #11 had 0.12% and 0.03% total impurities, respectively. Finally, after 2 week at 55° C.±2° C. and 40° C.±2° C. under 75%±5% RH, Formulation #12 had 0.08% and 0.02% total impurities, respectively. Concentrations of any excipient used in formulations did not exceed maximum allowable daily dose recommended in FDA's inactive ingredient list. The stability of each formulation showed that all the excipients used in the formulations were compatible with Ondansetron.

Example 6: In Vitro Permeability of Ondansetron Across Porcine Buccal Mucosa

Method

In vitro permeability of Ondansetron formulations across porcine buccal mucosa was evaluated to identify the formulations with better permeability and flux. A Franz diffusion apparatus and epithelial layers of porcine buccal mucosa were used to evaluate permeability. Heat separation method was used to collect the epithelia from the connective tissue and basal membrane of the mucosa. Specifically, a previously cut (1 inch×1 inch) mucosal membrane piece was placed into 65° C. phosphate buffered saline (PBS, pH 7.34) for two minutes, and then promptly removed and placed in a clear petri dish with a minimal amount of PBS. Afterwards, the connective tissue underneath was firmly held in place with a spatula and gently picked at the upper epithelia until it began to separate. Upon noticeable separation, the full edge was separated with a gentle practice across the tissue. Finally, the entire epithelia were pulled up and away from the lower dermis in small increments. Each epithelial membrane was placed between the 5 mm donor chamber and the receptor cell, and secured with clamps.

At the beginning of the study (i.e., time zero), 5 mL PBS was used as a receiver media and 0.5 mL of test formulation was loaded to the donor chamber. The membrane integrity was evaluated by the handheld Keysight LCR meter U1731C.

Subsequently, 0.2 mL of the sample was collected from the receptor cell at predetermined time intervals and immediately replaced with 0.2 mL of fresh PBS. Collected samples were filtered with a 0.45 μm Nylon membrane and then analyzed using an HPLC method.

Results

Permeability coefficient of Ondansetron HCl Dihydrate from formulations #O12 and #O13 (no permeability enhancer) was negligible, with a value of 1.13 and 0.13× $10^{-7}$ cm/sec, respectively. See Table 33. Surprisingly 2% caprylic acid in the formulation (#O14) improved the permeability coefficient to 5.32×$10^{-7}$ cm/sec. Inclusion of 1% cetylpyridinium chloride to the formulations did not make any difference in the permeability coefficients (#O3: 1.37 and #O4: 2.2×$10^{-7}$ cm/sec). See Table 31. A combination of 0.01% BAK and 2% caprylic acid improved the permeability coefficient of Ondansetron HCl Dihydrate by 13-fold (13.1×$10^{-7}$ cm/sec), compared to the control #O12 and by 6 fold over #O8 which has the same formulation except that #O2 contains BKC. Use of 30% glycerol (#O10) gave similar results as #O2. Furthermore, addition of 3% caprylic acid and no glycerol increased the permeability coefficient approximately 17-fold (17.8×$10^{-7}$ cm/sec), compared to the control (#O12). The combination of 0.5% menthol, 15% propylene glycol, 0.01% BKC, 2-3% caprylic acid and 40-41% alcohol improved the permeability coefficient of Ondansetron HCl Dihydrate at least 13 fold (#O1: 17.8, #O2: 13.1×$10^{-7}$ cm/sec). Hence, the results conclude that combination of 0.01% BKC, 0.5% Menthol and 2% caprylic acid is likely to enhance the permeability of Ondansetron HCl Dihydrate across the sublingual mucosa.

TABLE 31

In vitro permeability of Ondansetron sublingual spray formulations across the porcine buccal mucosa.

| Formulation | #O1 | #O2 | #O3 | #O4 (mixed with ethanol) | #O5 |
|---|---|---|---|---|---|
| Ondansetron HCl Dihydrate | 4.5581 | 4.5581 | 5.5 | 5.5 | 4.558 |
| Sucralose Micronized | 0.6 | 0.6 | — | — | 0.6 |
| L-Menthol | 0.5 | 0.5 | 1 | 1 | 0.5 |
| Propylene Glycol | 15 | 15 | — | — | — |
| Glycerol | — | — | — | — | 40 |
| Edetate disodium dihydrate (EDTA) | 0.001 | 0.001 | 43.5 | 43.5 | 0.001 |
| Benzalkonium Chloride (BKC) | 0.01 | 0.01 | — | — | — |
| Caprylic Acid | 3 | 2 | 2 | 2 | 2 |
| Cetylpyridinum chloride | — | — | 1 | 1 | — |
| Strawberry flavor nat & art 915.0543 U | 0.08 | 0.08 | — | — | 0.08 |
| Dehydrated Alcohol | 40 | 41 | 47 | 47 | 40 |
| Purified Water USP | QS | QS | QS | QS | QS |
| Total | 100 | 100 | 100 | 100 | 100 |
| Flux (μg/min/cm$^2$) | 5.8 | 4.33 | 0.45 | 0.73 | 1.83 |
| Permeability coefficient (×$10^{-7}$ cm/sec) | 17.8 ± 3.8 | 13.1 ± 1.9 | 1.37 ± 0.28 | 2.2 ± 0.9 | 7.46 ± 2.15 |

Components: % w/w
QS: quantity sufficient
Permeability coefficient: mean ± standard deviation

TABLE 32

In vitro permeability of Ondansetron sublingual spray formulations across the porcine buccal mucosa.

| Formulation | #O6 | #O7 | #O8 | #O9 | #O10 |
|---|---|---|---|---|---|
| Ondansetron HCl Dihydrate | 4.558 | 4.558 | 3.8 | 4.58 | 4.24 |
| Sucralose Micronized | 0.6 | 0.6 | 0.6 | 0.6 | 0.6 |
| L-Menthol | 0.5 | 0.5 | 0.5 | 0.5 | 0.5 |
| Propylene Glycol | — | — | 15 | 5 | — |
| Glycerol | 30 | 30 | — | 20 | 30 |
| Edetate disodium dihydrate (EDTA) | 0.001 | 0.001 | — | 0.001 | 0.001 |
| Benzalkonium Chloride (BKC) | — | — | — | 0.01 | 0.01 |

TABLE 32-continued

In vitro permeability of Ondansetron sublingual spray
formulations across the porcine buccal mucosa.

| Formulation | #O6 | #O7 | #O8 | #O9 | #O10 |
|---|---|---|---|---|---|
| Caprylic Acid | 2 | 2 | 2 | 2 | 2 |
| Strawberry flavor nat & art 915.0543 U | 0.08 | 0.08 | 0.08 | 0.08 | 0.08 |
| Dehydrated Alcohol | 50 | 40 | 41 | 50 | 50 |
| Purified Water USP | QS | QS | QS | QS | QS |
| Total | 100 | 100 | 100 | 100 | 100 |
| Flux (µg/min/cm$^2$) | 1.31 | 1.09 | 0.58 | 2.18 | 3.38 |
| Permeability coefficient (×10$^{-7}$ cm/sec) | 5.32 ± 0.61 | 4.44 ± 0.41 | 2.37 ± 0.4 | 8.88 ± 2.18 | 13.7 ± 2.14 |

Components: % w/w
QS: quantity sufficient
Permeability coefficient: mean ± standard deviation

TABLE 33

In vitro permeability of Ondansetron sublingual spray
formulations across the porcine buccal mucosa.

| Formulation | #O11 | #O12 | #O13 | #O14 | #O15 |
|---|---|---|---|---|---|
| Ondansetron HCl Dihydrate | 4.56 | 4.22 | 4.22 | 4.558 | 4.558 |
| Sucralose Micronized | 0.6 | 0.6 | 0.6 | 0.6 | 0.6 |
| L-Menthol | 0.5 | 0.05 | 0.05 | 0.5 | 0.5 |
| Propylene Glycol | 5 | 15 | 15 | — | — |
| Glycerol | — | — | — | 40 | 30 |
| Edetate disodium dihydrate (EDTA) | 0.001 | — | — | 0.001 | 0.001 |
| Benzalkonium Chloride (BKC) | 0.01 | — | — | — | — |
| Caprylic Acid | 2 | — | — | 2 | 2 |
| Cetylpyridinum chloride | — | — | — | — | — |
| Strawberry flavor nat & art 915.0543 U | 0.08 | — | — | 0.08 | 0.08 |
| Methyl paraben | — | — | 0.02 | — | — |
| Propyl paraben | — | — | 0.02 | — | — |
| Fruit punch flavor | — | — | 0.15 | — | — |
| Dehydrated Alcohol | 50 | 31.21 | 31.21 | 40 | 50 |
| Purified Water USP | QS | QS | QS | QS | QS |
| Total | 100 | 100 | 100 | 100 | 100 |
| Flux (µg/min/cm$^2$) | 0.71 | 0.37 | 0.04 | 1.31 | 0.58 |
| Permeability coefficient (×10$^{-7}$ cm/sec) | 2.14 ± 8.98 | 1.13 ± 0.53 | 0.13 ± 1.9 | 5.32 ± 6.13 | 2.37 ± 0.39 |

Components: % w/w
QS: quantity sufficient
Permeability coefficient: mean ± standard deviation

Example 7: Mini-Pig Pharmacokinetic Data for Ondansetron Formulations

Method

Protocol design was a single dose crossover study. Four or five healthy male Yucatan mini-pigs weighing approximately forty kilograms each were sublingually administered the Ondansetron formulations. The mini-pigs were fasted overnight until four hours post administration. Each dosing was followed by a one-week washout period. Blood samples were taken pre-dose and 3, 5, 10, 15, 20, 30 min, 1, 2, 4, 8 and 24 hours post dose. Mini-pig plasma samples were measured for Ondansetron concentrations via liquid chromatography-tandem mass spectrometry.

The following pharmacokinetic parameters were calculated: peak concentration in plasma ($C_{max}$), time to reach $C_{max}$ ($T_{max}$), and area under the concentration-time curve from time-zero to 24 hours post-dose ($AUC_{0-24h}$).

Results

The summary of Ondansetron pharmacokinetic parameters after single-dose sublingual administration of Ondansetron formulations to Yucatan mini-pigs under fasted conditions are summarized in Table 34. As shown, Formulations #O2M, #O4M, #O5M and #O6M, which include caprylic acid and replaced parabens with edetate disodium dihydrate and benzalkonium chloride (BKC) showed better pharmacokinetic performance, compared to Formulations #O1M and #O3M. Surprisingly, these formulations reached peak plasma concentration at least 7 times faster; achieved a much greater peak plasma concentration and achieved a greater area under the curve than Formulations #O1M and #O3M. Notably, Formulation #O5M reached geo-mean maximum plasma concentration of 8.9 ng/mL in only 3 minutes. See Table 35.

TABLE 34

Sublingual Ondansetron Formulations for Mini-pig Dosing

| Formulation | #O1M | #O2M | #O3M | #O4M | #O5M | #O6M |
|---|---|---|---|---|---|---|
| Dose | 8 mg (1 spray) | 6 mg (2 sprays) | 6 mg (2 sprays) | 6 mg (2 sprays) | 6 mg (2 sprays) | 5 mg (2 sprays) |
| Ondansetron HCl Dihydrate | 10.71 | 4.56 | 4.2229 | 4.1 | 4.24 | 3.72 |
| Sucralose, micronized | 1.00 | 0.60 | 0.6 | 0.6 | 0.6 | 0.60 |
| L-Menthol | 2.50 | 0.50 | 0.05 | 0.5 | 0.5 | 0.50 |
| Propylene glycol | — | 5.00 | 15 | — | — | 5.00 |
| Edetate disodium dihydrate (EDTA) | — | 0.001 | — | 0.001 | 0.001 | 0.001 |
| Benzalkonium Chloride (BKC) | — | 0.01 | — | 0.01 | 0.01 | 0.01 |
| Caprylic Acid | — | 2.00 | — | 2 | 2 | 2.00 |
| Strawberry flavor nat & art 915.0543 U | — | 0.08 | — | 0.08 | 0.08 | 0.08 |
| Purified Water USP | — | 37.25 | 48.73 | 12.709 | 12.569 | 38.089 |
| Dehydrated alcohol | 42.80 | 50.00 | 31.207 | 40 | 50 | 50.00 |
| Methyl Paraben | 0.10 | — | 0.02 | — | — | — |
| Propyl Paraben | 0.02 | — | 0.02 | — | — | — |
| Glycerin | 42.87 | — | — | 40 | 30 | — |
| Fruit punch Flavor MET 0003389 | — | — | 0.15 | — | — | — |
| BKC | — | — | — | 0.01 | 0.01 | — |
| Total | 100 | 100 | 100 | 100 | 100 | 100 |

Components: % w/w
QS: quantity sufficient
Permeability coefficient: mean ± standard deviation

TABLE 35

Geometric mean plasma concentrations for Ondansetron after sublingual administration of Ondansetron formulations to Yucatan mini-pigs under fasted conditions.

| Formulation | #O1M | #O2M | #O3M | #O4M | #O5M | #O6M |
|---|---|---|---|---|---|---|
| Concentration @ 3 min (ng/mL) | NC | 2.89 | 0 | 2.54 | 5.41 | 4.78 |
| Concentration @ 5 min (ng/mL) | 0 | 5.32 | 0.21 | 3.61 | 6.53 | 5.29 |
| Concentration @ 10 min (ng/mL) | 0.61 | 5.18 | 0.36 | 2.08 | 3.91 | 7.02 |
| Concentration @ 15 min (ng/mL) | 0.64 | 4.89 | 0.64 | 2.88 | 4.17 | 7.30 |
| Concentration @ 30 min (ng/mL) | 1.88 | 5.23 | 1.44 | 2.59 | 4.82 | 5.3 |
| $T_{max}$ (min) | 60 | 8 | 60 | 5 | 3 | 5 |
| $C_{max}$ (ng/mL) | 2.5 ± 1.9 | 8.2 ± 1.6 | 1.9 ± 2.5 | 4.7 ± 1.4 | 8.9 ± 2.5 | 14.3 ± 2.1 |
| $AUC_{0-24\,h}$ (ng*min/mL) | 340.6 ± 1.5 | 1165.3 ± 1.2 | 399.8 ± 2.1 | 567.7 ± 1.5 | 858.6 ± 1.2 | 1213.5 ± 1.4 |

NC: blood sample not collected
$T_{max}$: median value
$C_{max}$ and $AUC_{0-24\,h}$: geometric mean ± geometric SD

What is claimed is:

1. A sublingual spray formulation comprising:
   from about 3% to about 11% w/w ondansetron;
   from about 30% to about 60% w/w ethanol;
   from about 20% to about 48% w/w glycerin;
   from about 0.05% to about 0.5% w/w menthol; and
   from about 0.5% to about 5% w/w caprylic acid, wherein w/w denotes weight by total weight of the formulation.

2. The formulation of claim 1 wherein the formulation is a liquid.

3. The formulation of claim 1 wherein the formulation is substantially free of water.

4. The formulation of claim 1 wherein the formulation is free of propellant.

5. The formulation of claim 1 further comprising water.

6. The formulation of claim 1 further comprising a pharmaceutically acceptable sweetener.

7. The sublingual spray formulation of claim 1 wherein the formulation is capable of producing a droplet size distribution wherein:
   a) the mean Dv(10) is from about 10 to about 35 microns during administration;
   b) the mean Dv(50) is from about 40 to about 200 microns during administration; and c) the mean Dv(90) is from about 150 to about 700 microns during administration.

8. The sublingual spray formulation of claim 1 wherein the formulation is capable of producing a spray plume wherein:
   a) the mean ovality ratio is from about 1.0 to about 2.0 and
   b) the mean angle is from about 25 to about 65 degrees.

9. A sublingual spray formulation comprising:
   ondansetron at a concentration of about 4.24% w/w;
   ethanol at a concentration of about 50% w/w;
   glycerin at a concentration of about 30% w/w;
   menthol at a concentration of about 0.5% w/w; and
   caprylic acid at a concentration of about 2% w/w, wherein w/w denotes weight by total weight of the formulation.

10. The sublingual formulation of claim 9 further comprising:
    about 0.6% w/w sucralose;
    about 0.001% w/w edetate disodium dihydrate;
    about 0.01% w/w benzalkonium chloride; and
    about 0.08% w/w of strawberry flavor.

11. A method for treating or preventing nausea and emesis in humans associated with chemotherapy, radiation or surgery for cancer treatment comprising administering the formulation of claim 1 to a patient in need thereof.

12. The method of claim 11 wherein from about 50 to about 400 μL of the formulation of claim 1 is administered to the patient in need thereof.

13. The method of claim 12 wherein from about 100 to about 200 μL of the formulation of claim 1 is administered to the patient in need thereof.

14. A method for treating or preventing nausea and emesis in humans associated with chemotherapy, radiation or surgery for cancer treatment comprising administering the formulation of claim 4 to a patient in need thereof.

15. The method of claim 14 wherein from about 50 to about 400 μL of the formulation of claim 1 is administered to the patient in need thereof.

16. The method of claim 15 wherein from about 100 to about 200 μL of the formulation of claim 1 is administered to the patient in need thereof.

* * * * *